United States Patent [19]

Langley et al.

[11] Patent Number: 5,421,812

[45] Date of Patent: Jun. 6, 1995

[54] METHOD AND APPARATUS FOR CONTROLLING CONCENTRATIONS IN TUBING SYSTEM

[75] Inventors: Robert W. Langley, Westminster; Michael E. Schwab, Lakewood, both of Colo.

[73] Assignee: COBE Laboratories, Inc., Lakewood, Colo.

[21] Appl. No.: 845,677

[22] Filed: Mar. 4, 1992

[51] Int. Cl.[6] .................................................. A61M 1/00
[52] U.S. Cl. ........................................ 604/4; 604/65; 604/67
[58] Field of Search .................. 604/4, 5, 6, 65, 67, 604/19, 27, 403, 407

[56] References Cited

U.S. PATENT DOCUMENTS

| | | | |
|---|---|---|---|
| 3,916,892 | 11/1975 | Latham, Jr. | 604/6 |
| 4,447,191 | 5/1984 | Bilstad et al. | 604/122 |
| 4,458,539 | 7/1984 | Bilstad et al. | 604/6 |
| 4,481,827 | 11/1984 | Bilstad et al. | 604/6 |
| 4,501,531 | 2/1985 | Bilstad et al. | 604/123 |
| 4,540,406 | 9/1985 | Miles | 604/4 |
| 4,573,961 | 3/1986 | King | 604/6 |
| 4,648,866 | 3/1987 | Malbraneq et al. | 604/5 |
| 4,655,742 | 4/1987 | Vantard | 604/6 |
| 4,657,529 | 4/1987 | Prince et al. | 604/66 |
| 4,708,714 | 11/1987 | Larsson et al. | 604/6 |
| 4,736,748 | 4/1988 | Nakamura et al. | 604/4 |
| 4,769,001 | 9/1988 | Prince | 604/118 |
| 4,795,314 | 1/1989 | Prybella et al. | 604/6 |
| 4,850,995 | 7/1989 | Tie et al. | 604/6 |
| 4,850,998 | 7/1989 | Schoendorfer | 604/6 |
| 4,867,738 | 9/1989 | Mintz | 604/4 |
| 4,923,598 | 5/1990 | Schäl | 604/5 |
| 4,968,295 | 11/1990 | Neumann | 604/6 |
| 4,995,268 | 2/1991 | Ash et al. | 604/4 |
| 5,092,836 | 3/1992 | Polaschegg | 604/4 |
| 5,112,298 | 5/1992 | Prince et al. | 604/5 |

*Primary Examiner*—Sam Rimell
*Attorney, Agent, or Firm*—Beaton & Folsom

[57] ABSTRACT

A method and apparatus for determining, controlling or establishing the level of a constituent such as anticoagulant in a body fluid such as blood in a procedure for processing the fluid. The anticoagulant flow rate from an anticoagulant reservoir, the blood flow rate, the flow rate of collected fluid and the flow rate of replacement fluid are monitored, and an anticoagulant flow balance is established whereby the flow of anticoagulant into the donor or patient will be equal to the flow rate of anticoagulant out of the anticoagulant reservoir, plus the flow rate of anticoagulant from the donor or patient, plus the flow rate of anticoagulant in the replacement fluid, minus the flow rate of anticoagulant in the collect fluid. The flow rate of anticoagulant from the donor or patient can be determined based on the anticoagulant metabolic half-life, the volume of the donor's or patient's blood, and the amount and time of infusion of anticoagulant into the donor or patient.

32 Claims, 1 Drawing Sheet

METHOD AND APPARATUS FOR CONTROLLING CONCENTRATIONS IN TUBING SYSTEM

FIELD OF THE INVENTION

This invention relates to the field of fluid tubing systems and, in particular, relates to monitoring and controlling the flow rate and concentration of one or more constituents in a tubing system. The invention has particular application in controlling flow rates and concentrations of a constituent such as anticoagulant in a blood tubing set used in blood processing such as apheresis procedures and in the donor/patient to which the tubing set is connected.

BACKGROUND OF THE INVENTION

Various apheresis procedures require the use of anticoagulants such as acid citrate dextrose ("ACD") or heparin to prevent hemostasis and to permit blood processing. The rate of blood flow and, therefore, the time required to complete a procedure are related to the allowable anticoagulant level in the donor (in the case of a person donating a blood component) or in the patient (in the case of a person whose blood is being treated). If the anticoagulant level in the tubing set is too low, the blood will clot. If the anticoagulant level in the donor/patient is too high, adverse physiological reactions may occur. For example, ACD interferes with clotting by binding with ionized calcium, and excessive ACD levels can result in chills or convulsions. Heparin may cause flushing or hypotension, and its anticoagulant effects (it has a half life of about four hours) can last dangerously long after the procedure is completed. It is therefore desirable to carefully control the anticoagulant level.

In the past, anticoagulant levels have been controlled indirectly and imprecisely by controlling the rate of infusion of anticoagulant into the tubing set, without any direct control on the rate of infusion of anticoagulant into the donor/patient. That approach is not exact because it does not account for the anticoagulant that is removed from the tubing set by the procedure itself. The removed anticoagulant never enters the donor/patient. For example, a significant volume of anticoagulant is drawn off in the plasma collect line in plasma collection procedures and in the cell collect line in cell collection procedures. In addition, that approach does not account for anticoagulant added to the tubing set by the donor/patient due to the recirculation of unmetabolized anticoagulant from the donor/patient into the inlet line, nor does it account for anticoagulant added to the tubing set by the replacement fluid.

There are many prior art systems for controlling various flow rates in a tubing set, but it is believed that these systems are not applicable to the control of anticoagulant flow rates and concentrations in the manner of the present invention. For example, U.S. Pat. No. 4,582,598 by Bilstad discloses a system in which the collection rate and the replacement fluid rate are continuously monitored and adjusted by a control means that is responsive to measurement signals; U.S. Pat. Nos. 4,447,191 and 4,501,531 by Bilstad include a control circuit for adjusting the anticoagulant pump rate and for discontinuing the anticoagulant pumping in case a failsafe system detects an air bubble or other tripping event. It appears that none of these patents disclose a method for adjusting anticoagulant infusion rates to maintain a desired anticoagulant flow rate or concentration by considering the additive and subtractive effects of the tubing circuit or the recirculation of unmetabolized anticoagulant from the donor/patient.

U.S. Pat. No. 4,769,001 by Prince describes a system for calibrating an anticoagulant pump and a blood pump by monitoring the pressure in the line between the two pumps. Neither of these patents teaches a method for maintaining a desired anticoagulant flow rate or concentration by adjusting the anticoagulant infusion rate to account for variations caused by collection, replacement and recirculation.

U.S. Pat. No. 4,968,295 by Neumann discloses a blood separation apparatus in which centrifuge speeds are automatically varied in response to blood flow rates so that the volume ratios of the fractions remain constant. The apparatus includes an anticoagulant control wherein the anticoagulant infusion rate is varied as a linear function of the blood flow rate, but without considering collection, replacement or recirculation effects.

Other systems in which anticoagulant infusion rates may be directly or indirectly controlled include those described in U.S. Pat. Nos. 4,817,045 by Faeser; 4,923,598 by Schal; 4,655,742 by Vantard; 4,648,866 by Malbrancq; 4,573,961 by King; 4,795,314 by Prybella; 4,657,529 by Prince; and 4,995,268 by Ash. As in the other art described more particularly above, none of these teaches a method for varying the anticoagulant infusion rate to account for collection, replacement and withdrawal effects.

Anticoagulant levels can be expressed in several ways, including concentration, volume and flow rate. For purposes of this patent, "concentration" of anticoagulant refers to the volume fraction of anticoagulant in a fluid. "Flow rate" refers to the volume of flowing fluid per unit of time. As explained below, the important anticoagulant levels are typically the concentration of anticoagulant in the donor/patient and the flow rate and concentration of anticoagulant in the inlet line and the return line to the donor/patient. It will be apparent to those skilled in the art that these levels are related to one another and can be expressed in other terms (for example, the flow rate of anticoagulant in the return line can be expressed as the flow rate of fluid in the return line times the anticoagulant concentration in the return line). Unless otherwise specified, the term "level" in the claims will refer to any of, and any combination of, flow rate, concentration and volume. It will also be apparent to those skilled in the art that although it is convenient to express fluid quantities in terms of volume, the invention also includes quantities expressed in terms of weight by making appropriate adjustments to account for the specific gravities of the fluids.

SUMMARY OF THE INVENTION

The present invention includes an apparatus and method for maintaining a desired anticoagulant level in an apheresis tubing set and, particularly, in the inlet line and return line and in the donor/patient to which the return line is connected. The invention includes a method for determining the anticoagulant removed by various collect lines and the effect of the anticoagulant added by replacement fluid in the return line. By considering these effects, several important procedure-dependent variables can be determined and controlled, including the anticoagulant flow rate. Once the desired variables are determined, the anticoagulant infusion rate into the tubing set can be adjusted accordingly by a suitable controller such as a microprocessor-based controller coupled with a precision peristaltic pump.

Another embodiment of the invention considers the effect of unmetabolized anticoagulant recirculating from the donor/patient into the inlet line. The flow rate of unmetabolized anticoagulant in the inlet line can be determined in a process which takes into consideration the anticoagulant flow rate in the return line, the patient blood volume, the anticoagulant half-life, and the time of the procedure. This embodiment lends further precision to the process for determining anticoagulant levels because it accounts for anticoagulant build-up in the system, and it also aids in determining the total anticoagulant volume and concentration in the donor/patient.

The invention also has application outside the field of apheresis. It can be used in any other field in which a constituent is added to a flow stream having one or more divertive or additive flow streams, especially if the constituent is a material with a predictable decay rate.

In particular, the invention includes a method and apparatus for determining the anticoagulant level in a fluid tubing set used for processing blood from a donor/patient, and the anticoagulant level in the donor/patient, by determining the amount of anticoagulant added to the tubing set, determining the amount of anticoagulant removed from the tubing set, and subtracting the amount removed from the amount added. Further, the invention includes a method and apparatus for processing a body fluid with a tubing set having an inlet on the upstream end in communication with the body, an outlet on the downstream end in communication with the body, a constituent inlet between the tubing set inlet and outlet for adding constituent such as anticoagulant, and a fraction outlet for removing a fluid fraction between the constituent inlet and tubing outlet, by determining the flow rate of constituent in the tubing set between the constituent inlet and the fraction outlet and the flow rate of constituent through the fraction outlet, and determining the flow rate of constituent between the fraction outlet and the tubing set outlet by subtracting the flow rate through the fraction outlet from the flow rate between the constituent inlet and the fraction outlet. The flow rate of constituent into and out of the tubing set can be adjusted accordingly to maintain the constituent at a desired level.

DETAILED DESCRIPTION OF THE INVENTION

Figure 1:
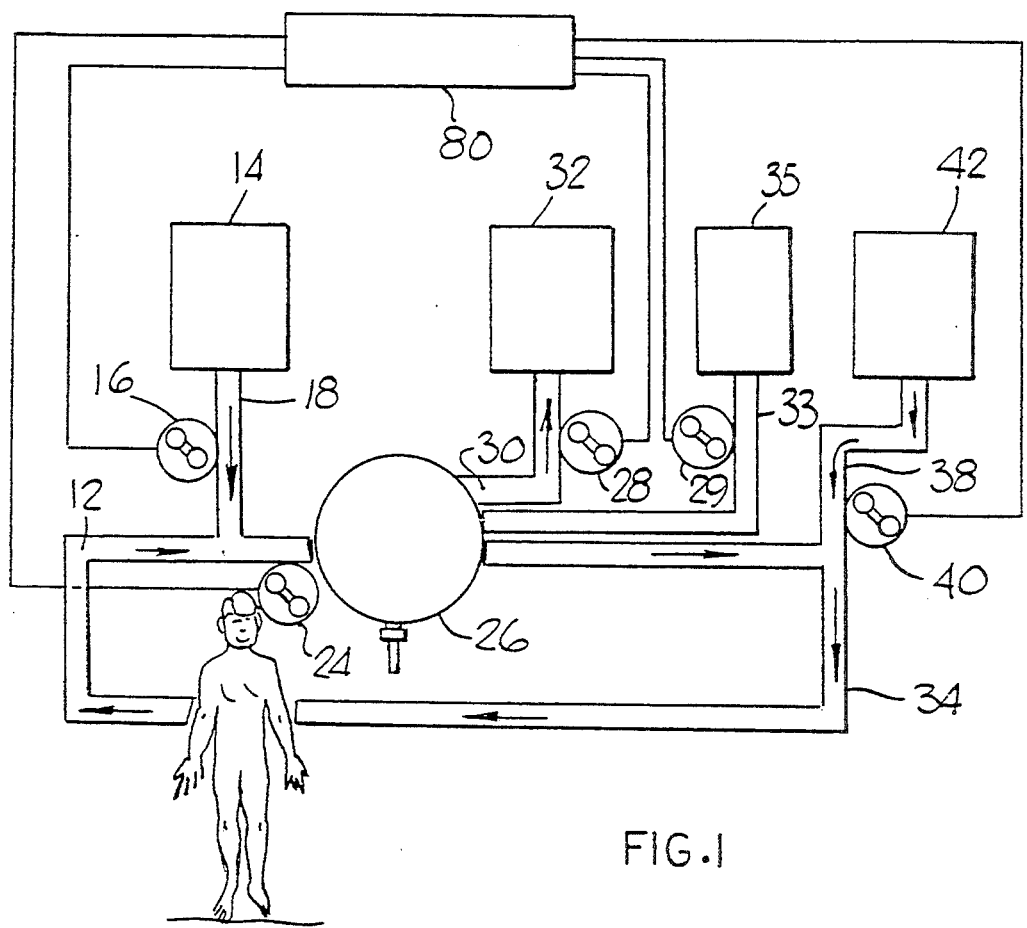
FIG. 1 shows the flow path for a hypothetical apheresis procedure where the invention is applicable.

The flow paths for a hypothetical blood apheresis procedure is shown in FIG. 1. The flow paths shown in FIG. 1 are not intended to depict any actual apheresis procedure, but instead are intended to present the flow paths for a variety of possible procedures. As explained below, actual procedures will generally not include all of the flow paths shown in FIG. 1.

Whole blood is removed from a donor/patient into an inlet line 12. An anticoagulant such as acid citrate dextrose ("ACD") or heparin is pumped from an anticoagulant reservoir 14 by an anticoagulant pump 16 through an anticoagulant line 18 in fluid communication with the inlet line 12. The whole blood with added anticoagulant is pumped by an inlet pump 24 to a centrifuge 26. The centrifuge 26 may be of the continuous flow type such as the centrifuge used with the SPECTRA brand apheresis system by COBE BCT, Inc.

The centrifuge 26 can fraction the whole blood into a variety of blood components such as plasma, platelets, white blood cells and red blood cells. The plasma may be drawn off by a plasma pump 28 to a plasma collect line 30 and into a plasma collect bag 32. Cells may be drawn off by a cell pump 29 to a cell collect line 33 and into a cell collect bag 35. A return line 34 returns to the donor/patient any components that are not collected. In fluid communication with the return line 34 is a replacement fluid line 38. A replacement fluid pump 40 pumps replacement fluid from a replacement fluid reservoir 42 into the replacement fluid line 38. The outlet end of the return line 34 enters the donor/patient. The flow through the various pumps can be monitored and controlled using a microprocessor based controller 80.

The flow through the system can be expressed as a generalized equation:

$$Q_{RP} = Q_P + Q_A + Q_{RF} - Q_C - Q_{PC}$$

where:
$Q_{RP}$ = plasma flow rate in the return line
$Q_P$ = plasma flow rate in the inlet line
$Q_A$ = anticoagulant flow rate through the anticoagulant line
$Q_{RF}$ = replacement fluid flow rate
$Q_C$ = cell collect flow rate
$Q_{PC}$ = plasma collect flow rate This equation can be expressed in terms of anticoagulant flow rates by multiplying each flow term by its respective anticoagulant concentration variable, with the assumption that the anticoagulant concentration in the anticoagulant line is one. The anticoagulant flow in the cell collect and plasma collect lines is equal to the total flow in those lines multiplied times the anticoagulant concentration in the flow entering the centrifuge (which is the sum of the plasma flow in the inlet line $Q_P$ and the anticoagulant flow $Q_A$) so that:

$$C_{RP}Q_{RP} = C_{DP}Q_P + Q_A + C_{RF}Q_{RF} - \frac{(Q_C + Q_{PC})(C_{DP}Q_P + Q_A)}{(Q_P + Q_A)}$$

where:
$C_{RP}$ = anticoagulant concentration in return line plasma
$C_{DP}$ = anticoagulant concentration in donor/patient plasma
$C_{RF}$ = anticoagulant concentration in replacement fluid This can be converted to blood-based variables so that:

$$Q_{IN} = (Q_{AR} + A[Q_{PC} + (1 - H_C)Q_C])/B$$

where:
$Q_{IN}$ = total inlet flow rate (combined blood and anticoagulant)
$Q_{AR}$ = specified anticoagulant flow rate through the return line
$H_C$ = hematocrit in cell collection line
$A = [C_{DB}(R-1)+1]/[R(1-H)+H] - C_{RF} F$
$B = C_{DB}(1-1/R) + (1-C_{RF})/R$
where:
$C_{DB}$ = anticoagulant concentration in donor/patient blood R = ratio of total inlet flow rate $Q_{IN}$ to anticoagulant flow rate $Q_A$
H = donor/patient hematocrit
F = ratio of fluid volume added to fluid volume removed in procedure These values can be calculated in real time to iteratively determine the desired variables whenever the parameters are changed.

It is noted that one of the variables in the equations set forth above is the anticoagulant concentration in the donor/patient blood $C_{DB}$. For procedures that last a short time and involve small volumes of blood there will be very little build-up of unmetabolized anticoagulant in the donor/patient, and this value can be taken as zero. For procedures that last a longer time and involve larger volumes, this value may be determined, preferably on a real-time basis. The rate of change of the volume of anticoagulant in the donor is:

$$\frac{dV_{AD}}{dt} = \frac{V_P \, dC_{DP}}{dt} = C_{RP} Q_{RP} - C_{DP} Q_P - K C_{DP} V_P$$

where:
$V_{AD}$ = volume of anticoagulant in donor blood
$V_P$ = volume of plasma in donor blood The term K is the anticoagulant metabolic decay constant which is related to the decay half life:

$$K = \ln 2 / t_{\frac{1}{2}}$$

where:
$t_{\frac{1}{2}}$ = anticoagulant half life

Substituting the anticoagulant flow equation previously set forth into the above equation for the rate of change of the volume of anticoagulant in the donor/patient:

$$\frac{dC_{DP}}{dt} = a - b\, C_{DP}$$

where:
$a = (1/V_P)[Q_A(1-(Q_C+Q_{PC})/(Q_P+Q_A)) + C_{RF} Q_{RF}]$
$b = (Q_P/V_P)[(Q_C+Q_{PC})/(Q_P+Q_A)] + K$ If this equation expressing the rate of change of the concentration of anticoagulant as a function of time is integrated over time, then:

$$C_{DB} = M_t(1 - e^{-N_t})$$

where $$M_t = \frac{[1 - (V_C + V_{PC})/((1-H)V_{BP} + V_A)](V_A/V_B) + C_{RF}V_{RF}/V_B}{N_t}$$

$N_t = (V_{BP}/V_B)[(V_C + V_{PC})((1-H)V_{BP} + V_A)] + Kt$
$V_C$ = volume of cells collected
$V_{PC}$ = volume of plasma collected
H = hematocrit of donor/patient
$V_{BP}$ = volume of blood processed
$V_A$ = volume of anticoagulant pumped
$V_B$ = volume of donor/patient's blood
t = time
$V_{RF}$ = volume of replacement fluid added to the tubing set As mentioned above, this set of equations and the schematic diagram of FIG. 1 which corresponds to the equations do not necessarily portray any real procedure, but are only presented as a generalized hypothetical procedure. In most real procedures, one or more of the variables of the equations will be zero because there will be no flow in one or more of the flow channels shown in the FIGURE. For example, in therapeutic plasma exchange, it can be appreciated that cells are not normally collected. Therefore, the variables for the volume of cells collected $V_C$ and the cell collect flow rate $Q_C$ will be zero.

Similarly, in cell collection procedures such as platelet collection, white blood cell collection and red blood cell collection, the collected plasma is returned to the donor/patient. Therefore, the variables for volume of plasma collected $V_{PC}$ and collected plasma flow rate $Q_{PC}$ will be zero. Also, for these procedures there may or may not be any replacement fluid added. If no replacement fluid is added, then the volume of replacement fluid $V_{RF}$ and the replacement fluid flow rate $Q_{RF}$ become zero.

It can be appreciated that other flow configurations may result in other variables becoming zero, thereby simplifying the determinations in other ways. Similarly, other flow configurations may result in the addition of other variables if other collect procedures are used or if other replacement fluids are added.

These variables can be monitored and calculated continuously by a microprocessor associated with the controller 80. The controller 80 can then adjust the pump rates to maintain desired parameters. For example, it is typically desired that the anticoagulant level in the centrifuge be kept at a high level to permit large flow rates but not so high that anticoagulant levels in the return line or in the donor/patient become uncomfortably high. These opposing goals can be met by determining and controlling the anticoagulant levels in the return line or in the donor/patient by adjusting the flow rate of anticoagulant from the anticoagulant reservoir and the flow rate of inlet blood. Other parameters can be similarly monitored and controlled to maintain optimum operating efficiency while ensuring the safety of the donor/patient.

The description herein contemplates numerical calculations of anticoagulant levels for the purpose of monitoring or adjusting (or both) the anticoagulant levels. It will be apparent that actual numerical calculations may not be necessary to utilize the invention. Instead, for example, the invention may be used to make relative adjustments to various flow rates depending on various other flow rates and parameters so that anticoagulant levels are optimally established even though they are never actually quantified. Such procedures are intended to be within the scope of the claims.

What is claimed is:

1. A method for establishing the anticoagulant level in a system including a tubing set in fluid communication with a donor or patient, comprising establishing the addition of anticoagulant to the tubing set; establishing the removal of anticoagulant from the tubing set; subtracting the removal of anticoagulant from the addition of anticoagulant to establish the anticoagulant level; and determining at a time after metabolism of the anticoagulant has begun the unmetabolized anticoagulant level in the donor or patient, based at least in part on the anticoagulant level in the tubing set.

2. The method of claim 1, wherein anticoagulant is infused into the tubing set at an infusion rate, the donor's or patient's blood flows into the tubing set at a blood flow rate, a blood constituent is withdrawn from the tubing set at a withdrawal rate, and replacement fluid flows into the tubing set at a replacement fluid flow rate, and further comprising adjusting at least one of the rate of infusion of anticoagulant into the tubing set, the rate of flow of the donor's or patient's blood into the tubing set, the rate of withdrawal of a blood constituent from the tubing set, and the rate of flow of replacement fluid into the tubing set, in response to the determined anticoagulant level.

3. The method of claim 2, wherein said adjustment is accomplished by programmable computing means.

4. The method of claim 3, wherein said programmable computing means includes a microprocessor in electronic communication with at least one fluid pump that controls at least one of said rates.

5. The method of claim 1, wherein the step of determining the addition of anticoagulant to the tubing set includes determining the infusion of anticoagulant from an anticoagulant reservoir into the tubing set.

6. A method for establishing the anticoagulant level in a system including a tubing set in fluid communication with a donor or patient, comprising establishing the addition of anticoagulant to the tubing set; establishing the removal of anticoagulant from the tubing set; subtracting the removal of anticoagulant from the addition of anticoagulant to establish the anticoagulant level; and determining the anticoagulant level in the donor or patient, based at least in part on the anticoagulant level in the tubing set; wherein anticoagulant is infused into the tubing set at an infusion rate, the donor's or patient's blood flows into the tubing set at a blood flow rate, a blood constituent is withdrawn from the tubing set at a withdrawal rate, and replacement fluid flows into the tubing set at a replacement fluid flow rate, and further comprising adjusting at least one of the rate of infusion of anticoagulant into the tubing set, the rate of flow of the donor's or patient's blood into the tubing set, the rate of withdrawal of a blood constituent from the tubing set, and the rate of flow of replacement fluid into the tubing set, in response to the determined anticoagulant level; wherein blood with anticoagulant is returned to the donor or patient by a return line, and wherein said adjustment is such that the anticoagulant flow rate in the return line does not exceed a predetermined maximum.

7. The method of claim 6, wherein said adjustment is such that the anticoagulant concentration in the blood processor does not fall below a predetermined minimum.

8. A method for establishing the anticoagulant level in a system including a tubing set in fluid communication with a donor or patient, comprising establishing the addition of anticoagulant to the tubing set; establishing the removal of anticoagulant from the tubing set; subtracting the removal of anticoagulant from the addition of anticoagulant to establish the anticoagulant level; and determining the anticoagulant level in the donor or patient, based at least in part on the anticoagulant level in the tubing set; wherein anticoagulant is infused into the tubing set at an infusion rate, the donor's or patient's blood flows into the tubing set at a blood flow rate, a blood constituent is withdrawn from the tubing set at a withdrawal rate, and replacement fluid flows into the tubing set at a replacement fluid flow rate, and further comprising adjusting at least one of the rate of infusion of anticoagulant into the tubing set, the rate of flow of the donor's or patient's blood into the tubing set, the rate of withdrawal of a blood constituent from the tubing set, and the rate of flow of replacement fluid into the tubing set, in response to the determined anticoagulant level; wherein blood with anticoagulant is returned to the donor or patient by a return line, and wherein said adjustment is such that at least one of the anticoagulant volume and anticoagulant concentration in the donor or patient does not exceed a predetermined maximum.

9. A method for establishing the anticoagulant level in a system including a tubing set in fluid communication with a donor or patient, comprising establishing the addition of anticoagulant to the tubing set; establishing the removal of anticoagulant from the tubing set; subtracting the removal of anticoagulant from the addition of anticoagulant to establish the anticoagulant level; and determining the anticoagulant level in the donor or patient, based at least in part on the anticoagulant level in the tubing set; wherein the step of determining the addition of anticoagulant to the tubing set includes determining the infusion of anticoagulant from an anticoagulant reservoir into the tubing set; and wherein the step of determining the addition of anticoagulant to the tubing set includes determining the infusion of anticoagulant from a replacement fluid reservoir into the tubing set.

10. The method of claim 9, wherein the step of determining the infusion of anticoagulant from a replacement fluid reservoir includes multiplying the rate of infusion of replacement fluid into the tubing set times the concentration of anticoagulant in the replacement fluid.

11. A method for establishing the anticoagulant level in a system including a tubing set in fluid communication with a donor or patient, comprising establishing the addition of anticoagulant to the tubing set; establishing the removal of anticoagulant from the tubing set; subtracting the removal of anticoagulant from the addition of anticoagulant to establish the anticoagulant level; and determining the anticoagulant level in the donor or patient, based at least in part on the anticoagulant level in the tubing set; wherein the step of determining the addition of anticoagulant to the tubing set includes determining the infusion of anticoagulant from an anticoagulant reservoir into the tubing set; and wherein the step of determining the removal of anticoagulant from the tubing set includes determining the rate of removal of anticoagulant in a collect fluid into a collect fluid reservoir.

12. The method of claim 11, wherein said step of determining the rate of removal of anticoagulant into a collect fluid reservoir includes multiplying the rate of removal of the collect fluid into the collect fluid reservoir times the concentration of anticoagulant in said collect fluid.

13. A method for establishing the anticoagulant level in a system including a tubing set in fluid communication with a donor or patient, comprising establishing the addition of anticoagulant to the tubing set; establishing the removal of anticoagulant from the tubing set; subtracting the removal of anticoagulant from the addition of anticoagulant to establish the anticoagulant level; and determining the anticoagulant level in the donor or patient, based at least in part on the anticoagulant level in the tubing set; wherein the step of determining the addition of anticoagulant to the tubing set includes determining the infusion of anticoagulant from an anticoagulant reservoir into the tubing set; and wherein such step of determining the anticoagulant added to the tubing set includes determining the level of anticoagulant in the blood from the donor or patient to be processed that enters the tubing set.

14. The method of claim 13, wherein the infused anticoagulant gradually metabolizes to produce a metabolized amount and an unmetabolized amount, and wherein said step of determining the level of anticoagulant in the donor's or patient's blood includes determining the unmetabolized amount.

15. The method of claim 14, a known amount of the donor's or patient's blood is processed through the tubing set, and wherein said step of determining the amount of anticoagulant that has not metabolized added to the donor or patient from the tubing set includes the use of an equation wherein the concentration of anticoagulant in the donor's or patient's blood is an exponential function of at least one of amount of anticoagulant added to the donor or patient, amount of blood in the donor or patient, amount of anticoagulant removed from the donor's or patient's blood, volume of donor's or patient's blood processed, concentration of anticoagulant in the fluid added to the tubing set, volume of fluid added to the tubing set, hematocrit of the donor or patient, and half life of the anticoagulant.

16. The method of claim 15, wherein said exponential equation is of the form:

$$C_{DB} = M_t(1 - e^{-N_{178}});$$

where
$C_{CB}$ = concentration of anticoagulant in donor or patient's blood $$M_t = \frac{(V_A/V_B)[1 - (V_C + V_{PC})/((1-H)V_{BP} + V_A)] + C_{RF}V_{RF}/V_B}{N_t}$$

$N_t = (V_{BP}/V_B)[(V_C + V_{PC})/((1-H)V_{BP} + V_A)] + Kt$
$V_A$ = volume of anticoagulant added to tubing set
$V_B$ = volume of blood in the donor or patient
$V_C$ = volume of cells collected out of the tubing set
$V_{PC}$ = volume of plasma collected out of the tubing set
H = donor's or patient's hematocrit
$V_{BP}$ = volume of donor or patient's blood processed
$C_{RF}$ = concentration of anticoagulant in replacement fluid added to the tubing set
$V_{RF}$ = volume of replacement fluid added to the tubing set
K = an anticoagulant metabolism constant
t = time.

17. The method of claim 16, wherein the metabolism constant K is related to the anticoagulant metabolic half-life.

18. The method of claim 17, wherein the metabolism constant is of the form:

$$K = \ln 2 / t_{\frac{1}{2}}$$

where
K = an anticoagulant metabolism constant
$t_{\frac{1}{2}}$ = metabolic half-life of the anticoagulant.

19. A method for establishing the anticoagulant level in a system including a tubing set in fluid communication with a donor or patient, comprising establishing the addition of anticoagulant to the tubing set; establishing the removal of anticoagulant from the tubing set; subtracting the removal of anticoagulant from the addition of anticoagulant to establish the anticoagulant level; and determining the anticoagulant level in the donor or patient, based at least in part on the anticoagulant level in the tubing set; wherein the coagulant is added to the tubing set of a known rate, and further comprising determining the volume of anticoagulant in the donor or patient by integrating over time the rate of addition of anticoagulant to the donor or patient minus the rate of removal of anticoagulant from the donor or patient.

20. The method of claim 19, wherein said tubing set includes an inlet line through which plasma moves from the donor or patient to the tubing set and a return line through which plasma moves from the tubing set to the donor or patient, and wherein said step of determining the volume of anticoagulant in the donor or patient is by an integral of an equation substantially of the form:

$$\frac{dV_{AD}}{dt} = C_{RP}Q_{RP} - C_{DP}Q_P - KC_{DP}V_P$$

where
$V_{AD}$ = volume of anticoagulant in the donor's or patient's blood
$C_{RP}$ = anticoagulant concentration in the return line plasma
$Q_{RP}$ = plasma flow rate in the return line
$C_{DP}$ = anticoagulant concentration in the donor's or patient's plasma
$Q_P$ = plasma flow rate in the inlet line
$V_P$ = volume of plasma in the donor's or patient's blood, 21. A method for establishing the anticoagulant level in a system including a tubing set in fluid communication with a donor or patient, comprising establishing the addition of anticoagulant to the tubing set; establishing the removal of anticoagulant from the tubing set; subtracting the removal of anticoagulant from the addition of anticoagulant to establish the anticoagulant level; and determining the anticoagulant level in the donor or patient, based at least in part on the anticoagulant level in the tubing set; wherein said tubing set may include a cell collect line through which collected cells flow, and wherein said steps is by an equation substantially of the form:

$$Q_{IN} = (Q_{AR} + A[Q_{PC} + (1 - H_C)Q_C])/B$$

where
$Q_{IN}$ = total rate of flow of donor's or patient's blood and anticoagulant into the tubing set
$Q_{PC}$ = rate of flow of collected plasma
$H_C$ = hematocrit in cell collection line
$Q_C$ = cell collect flow rate
$A = [C_{DB}(R-1) + 1]/[R(1-H) + H] - C_{RF}F$
$B = C_{DB}(1 - 1/R) + (1 - C_{RF})/R$ R = ratio of total rate of flow into the tubing set to rate of anticoagulant flow into tubing set
 = $Q_{IN}/Q_A$ $C_{DB}$ = concentration of anticoagulant in donor's or patient's blood
H = hematocrit of donor's or patient's blood
$C_{RF}$ = anticoagulant concentration in replacement fluid added to tubing set
$Q_{AR}$ = specified anticoagulant flow rate in the return line F = ratio of fluid volume added to, to fluid volume removed from, tubing set.

22. A method for processing a body fluid using a tubing set having an inlet on the upstream end in fluid communication with the body, an outlet on the downstream end in fluid communication with the body, a constituent inlet in fluid communication with the tubing set for adding a constituent to the body fluid, and a fraction outlet for removing a fluid fraction from the body fluid downstream from the constituent inlet and upstream from the outlet end, comprising determining the flow rate of constituent between the constituent inlet and the fraction outlet; determining the flow rate of constituent out of the fraction outlet; determining the flow rate of constituent between the fraction outlet and the tubing set outlet by subtracting the flow rate of constituent out of the fraction outlet from the flow rate of constituent between the constituent inlet and the fraction outlet, and adjusting the flow rate of constituent into and out of the tubing set to maintain a desired constituent flow rate between the fraction outlet and the tubing set outlet.

23. The method of claim 22, wherein said desired constituent flow rate is based upon the constituent level in the donor or patient.

24. The method of claim 23, wherein said constituent level in the body is determined with reference to at least one of the amount of such body fluid in the body, the amount of body fluid processed, and the amount of constituent flowing into the body.

25. The method of claim 24, wherein said constituent decays in the body over time and said constituent level in the body is determined with reference to the time the constituent has been in the donor or patient.

26. A system for controlling the level of anticoagulant infused into a donor or patient in a blood processing procedure, comprising: a blood tubing set having an inlet for establishing fluid communication with the donor's or patient's blood and an outlet for establishing fluid communication with the donor's or patient's blood, an anticoagulant source in communication with the tubing set, a blood fractionalizer in communication with the tubing set, a blood flow rate monitor to monitor the blood flow rate through the inlet of the tubing set, an anticoagulant flow rate monitor to monitor the anticoagulant flow rate through the anticoagulant source, at least one fraction flow rate monitor to monitor a blood fraction flow rate from the blood fractionalizer, and a processor for using at least one of said monitors to determine at least one of the anticoagulant flow rate through the tubing set outlet, the anticoagulant concentration in the tubing set outlet, and the total flow of anticoagulant through the tubing set outlet over a predetermined period of time.

27. The system of claim 26, wherein said processor determines the flow rate of anticoagulant through the tubing set outlet by subtracting the flow rate of anticoagulant out of the blood fractionalizer from the flow rate of anticoagulant between the anticoagulant source and the blood fractionalizer.

28. The system of claim 27, wherein said processor further determines the flow rate of anticoagulant through the tubing set outlet by considering the flow rate of anticoagulant through the tubing set inlet.

29. The system of claim 27, further comprising a replacement fluid source in communication with the tubing set, and wherein the processor further determines the flow rate of anticoagulant through the tubing set outlet by considering the flow rate of anticoagulant through the replacement fluid source in communication with the tubing set.

30. The system of claim 26, wherein said processor includes a microprocessor.

31. The system of claim 26, further comprising a flow rate controller to control the flow rate of at least one of the flow through the tubing set inlet, the flow through the anticoagulant source, and the flow out of the tubing set outlet, to produce a desired level of at least one of the flow rate of the anticoagulant out of the tubing set outlet, the concentration of anticoagulant flowing out of the tubing set outlet, the total flow of anticoagulant through the tubing set outlet, and the concentration of anticoagulant in the donor or patient.

32. A method for controlling the anticoagulant level in a system including a tubing set used for processing blood from a donor or patient using a blood processor, comprising determining the addition of anticoagulant to the tubing set; determining the removal of anticoagulant from the tubing set; subtracting the removal of anticoagulant from the addition of anticoagulant; determining the level of the unmetabolized anticoagulant in the donor or patient at a time after metabolism of said anticoagulant has begun; and controlling the anticoagulant level in the donor or patient, based at least in part on the determined anticoagulant level in the tubing set.

* * * * *